(12) United States Patent
Roulston et al.

(10) Patent No.: US 7,303,600 B2
(45) Date of Patent: *Dec. 4, 2007

(54) UNEXPANDED PERLITE ORE POLISHING COMPOSITION AND METHODS

(75) Inventors: John S. Roulston, Lompoc, CA (US); Dean Klein, Solvang, CA (US)

(73) Assignee: Advanced Minerals Corporation, Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/422,273

(22) Filed: Apr. 24, 2003

(65) Prior Publication Data

US 2003/0224702 A1 Dec. 4, 2003

Related U.S. Application Data

(60) Provisional application No. 60/375,738, filed on Apr. 25, 2002.

(51) Int. Cl.
*B24B 1/00* (2006.01)
*B24C 1/00* (2006.01)
*B24C 1/08* (2006.01)

(52) U.S. Cl. .................. 51/307; 451/28; 451/36; 451/41; 451/38; 451/42; 216/96

(58) Field of Classification Search ............... 51/307; 106/3, 35, DIG. 2; 424/49; 451/28, 36, 451/38, 75, 41, 42; 510/109, 395, 396, 397; 216/96

See application file for complete search history.

(56) References Cited

U.S. PATENT DOCUMENTS

| | | | |
|---|---|---|---|
| 2,696,049 A | 12/1954 | Black | 32/58 |
| 4,396,525 A * | 8/1983 | Rubin et al. | 510/397 |
| 5,124,143 A | 6/1992 | Muhlemann et al. | 424/49 |
| 5,266,304 A * | 11/1993 | Baffelli et al. | 424/49 |
| 5,395,541 A | 3/1995 | Carpenter et al. | 510/363 |
| 5,597,553 A | 1/1997 | Baffelli et al. | 424/49 |
| 5,810,587 A | 9/1998 | Bruns et al. | 433/88 |
| 5,840,090 A | 11/1998 | Ho et al. | 51/295 |
| 5,891,473 A | 4/1999 | Stanier | 424/489 |
| 5,928,719 A | 7/1999 | Mishima et al. | 427/180 |
| 5,976,506 A * | 11/1999 | Vernon | 424/49 |
| 6,083,001 A | 7/2000 | Deardon et al. | 433/88 |
| 6,139,820 A | 10/2000 | Fischer et al. | 424/52 |
| 6,235,824 B1 | 5/2001 | Vander et al. | 524/278 |
| 6,280,707 B1 | 8/2001 | Peterson et al. | 424/49 |

FOREIGN PATENT DOCUMENTS

| | | |
|---|---|---|
| CH | 531881 A | 12/1972 |
| GB | 2272640 A | 5/1994 |
| JP | 02 166189 | 6/1990 |
| WO | 94 15577 A | 7/1994 |
| WO | 96 09034 A1 | 3/1996 |
| WO | WO 9609034 * | 3/1996 |
| WO | 97 30126 A | 8/1997 |
| WO | 00 74638 A | 12/2000 |

OTHER PUBLICATIONS

Pages 444 through 453, Kirk-Othmer Encyclopedia of Chemical Technology, John Wiley & Sons, 1996 4th Edition, vol. 19 (the "Chemical Technology, vol. 19 Reference"), no month.

Pages 17 through 37, Kirk-Othmer Encyclopedia of Chemical Technology, John Wiley & Sons, 1991 4th Edition, vol. 1 (the "Chemical Technology, vol. 1 Reference"), no month.

Appendix A, Natural Glasses and Macerals, pp. 540 through 542, Mineralogy, W. H. Freeman aand Company, 2nd Edition, (the "Mineralogy Reference"), no date.

Pages 371 through 511, Handbook of Industrial Materials, Elsevier Advanced Technology, 2nd Edition (the "Industrial Materials Reference"), no date.

Harborlite Perlite, Technical Data Sheet, One (1) Page, Harborlite Perlite Grade P4 1000, no date.

Perlite Information Search, 41 Pages, INCON Corporation, Downloaded from Perlite.com on Mar. 2, 2002.

Perlite Market Study for British Columbia, pp. 1-11 and 24-26, Prepared by D.F. Gunning. P. Eng. and McNeal & Associates Consultants Ltd., British Columbia, Ministry of Energy, Mines and Petroleum Resources, Geological Survey Branch, Open File 1994, Mar. 21, 1994.

(Continued)

*Primary Examiner*—Michael Marcheschi
(74) *Attorney, Agent, or Firm*—Finnegan, Henderson, Farabow, Garrett & Dunner, L.L.P.

(57) ABSTRACT

An unexpanded perlite ore polishing composition is shown. The composition comprises base material having grains of unexpanded perlite ore of a selected distribution of particle sizes which undergo fracturing of the grains as a function of an abrasive force applied to the base material. The selected distribution of particle sizes includes a significant volume of grains of unexpanded perlite ore having a ($d_{90}$) particle size in a range of about 101 to about 229 μm. The base material is responsive to an abrasive force being applied thereto during polishing resulting in continued fracturing of the grains of unexpanded perlite ore to yield a final polishing composition having a sufficiently low level of abrasiveness under said abrasive force making it suitable for use in polishing. Compositions for polishing acrylic dentures and CRT tube surfaces using the unexpanded perlite ore polishing composition and methods for polishing the same are also shown.

20 Claims, 5 Drawing Sheets

OTHER PUBLICATIONS

Standard Practice Guide for Preparing Coal Samples for Microscopical Analysis by Reflected Light, Designation: D2797-85 (Reapproved 1999), pp. 1 through 4, American Society for Testing and Materials (the "ASTM Microscopical Analysis Reference"), no month.

Pages 1 through 10 of the Standard Guide for Preparation of Plastics and Polymeric Specimens for Microstructural. Examination, Designation :E 2015-99, American Society for Testing and Materials (the "ASTM Standard Guide Reference"), no date.

Product Information Sheet, One (1) Page, Paste, 3M(TM) CLINPRO(TM) Prophy, 3M Company 1995, no month.

Product Information Shhet, One (1) Page, Prophy Products. Whitehill Manufacturing, Inc., 2000, no month.

*Self-Adjusting Abrasiveness: a New Technology for Prophylaxis Pastes*; Lutz F. et al; pp. 53-63, vol 4, Quintessence International, Germany, Jan. 1993.

*Effects of Four Prophylaxis Pastes on Surface Roughness of a Composite, A Hybrid Ioner and A Compomer Restorative Material*; Warren Donna P. et al; pp. 245-251, vol. 4; Journal of Esthetic and Restorative Dentistry: Official Publication of American Academy of Esthetic Dentistry et al, 2002, no month.

Abstract— XP002262005 & JP 02 166190A, *Glass Type Polishing Material Preparation*; One (1) Page; (KYOR-N) Kyoritsu Yogyo Genryo KK, Section, Chapter Week 199031, Derwent Publications Ltd, London, GB, Jun. 26, 1990.

\* cited by examiner

UNEXPANDED PERLITE ORE POLISHING COMPOSITION AND METHODS

CROSS-REFERENCES TO RELATED APPLICATIONS

This Application claims the benefit, under Title 35, United States Code §119(e), of U.S. Provisional Patent Application Ser. No. 60/375,738 filed Apr. 25, 2002.

STATEMENT REGARDING FEDERALLY SPONSORED RESEARCH OR DEVELOPMENT

Not Applicable

REFERENCE TO A "MICROFICHE APPENDIX" (SEE 37 CFR 1.96)

Not Applicable

BACKGROUND OF THE INVENTION

1. Field of the Invention

The present invention relates to a unexpanded perlite ore polishing composition and method for polishing selected materials wherein an unexpanded perlite ore composition having grains of a selected distribution of particle sizes resulting in continued fracturing of the grains subject to an abrasive force applied to the composition during polishing. This results in an increase in the number of grains of unexpanded perlite ore having a smaller particle size than the selected distribution of particle sizes for efficient polishing and more particularly relates to a unexpanded perlite ore polishing composition and method for selectively abrading and polishing polymers, including acrylic polymers, dentures and other parts, components and articles fabricated from materials suitable for polishing with unexpanded perlite ore including optical glass, lenses and cathode ray tubes (CRT) surfaces subject to an abrasive force.

2. Description of the Prior Art

It is known in the art to use granular compositions for abrasion and polishing of the surfaces of an article.

Certain applications utilize pumice as an abrasive material or as an abrasive material additive to a polishing composition. Pumice is a rock froth formed by the extreme puffing of liquid lava by expanding gases liberated from solution in the lava prior to and during solidification. Pumice and pumicite are porous, glassy forms of lava, rich in silica. Both plumice, the massive form, and pumicite, the powder or dust form, have been widely used as a mild abrasive for polishing operations.

FIGS. 1 and 2 labeled "Prior Art" are scanning electron micrographs of pumice grains at magnifications of 100× and 300×, respectively. As depicted in the micrographs of FIGS. 1 and 2, the grains or particles of pumice have a plurality of large pores, or more specifically vesicles, that are an essential part to the definition of rock type. The large pores are separated by a plurality of substantially parallel planes with sharp edges or strata defining the structure thereof. The pumice, when used as an abrasive in a polishing material, typically generates scratches which is generally undesirable. The scratches are formed in the surface of an article by the aforementioned sharp edges of the pumice grains. Scratches generally require additional polishing using a fine polishing composition to remove the same and to polish the surface of the article to the desired finish.

A polish composition and method of use which utilizes suitable mild abrasives, such as pumice, are disclosed in U.S. Pat. No. 6,235,824.

It is also known in the art to use abrasive material in combination with individual grains of pumice in coated abrasive articles comprised of a backing having a layer of grains adherently bonded thereto by a binding material, an example of which is disclosed in U.S. Pat. No. 5,840,090.

It is also known in the art to have a granular composition which utilizes pumice as a part thereof, an example of which is disclosed in U.S. Pat. No. 5,891,473.

It also known in the art that toothpaste can be formulated to include a lightweight, low density solid filler such as expanded perlite as disclosed in U.S. Pat. No. 6,139,820.

It is also known in the art to utilize low-density expanded perlite as an abrasive in toothpaste as disclosed in U.S. Pat. No. 5,597,553. Specifically, U.S. Pat. No. 5,597,553 discloses a specific use of an expanded perlite in toothpaste which disintegrates when subjected to small mechanical stress, e.g., under the conditions of tooth brushing, into smaller, sharp-edged particles and that the same are well suited as a cleaning body in the toothpaste. U.S. Pat. No. 5,597,553 further discloses that the relatively course particles of expanded perlite have a size of the order of about 1 µm to 150 µm, the major portion being of about 20 µm. The expanded perlite particles are disclosed as performing a very short-lasting, but intensive cleaning action and are immediately comminuted into still finer particles which then perform a desired, mild polishing action down to a fine polishing. In U.S. Pat. No. 5,597,553, the specification recites that only the exploded (expanded) perlite is used in the toothpaste disclosed therein.

Toothpastes utilizing an expanded perlite are also disclosed in U.S. Pat. Nos. 5,597,553 and 5,124,143.

It is also known in the art to utilize exploded (expanded) perlite in a water-free prophylectic paste containing expanded perlite as disclosed in U.S. Pat. No. 6,139,820.

It is also known in the art that a cleaning composition containing a type II endoglycosidase includes an expanded perlite abrasive as a part thereof as disclosed in U.S. Pat. No. 5,395,541.

It is also known in the art to use a blend of polishing and cleaning agents in a prophylaxis procedure for stain removal and polishing of teeth. Such a blend of polishing and cleaning agents are generally known as prophy paste and may include fluoride ions. Certain of the known prophy paste use expanded perlite and pumice as grit material in the prophy paste. Examples of prophy paste using expanded perlite and pumice are the 3M brand prophy pastes known as 3M™ CLINPRO™ prophy paste and NUPRO® brand prophy paste sold by DENTSPLY. Other known prophy paste products are sold by WhiteHill Manufacturing, Inc. under the trademark Professional Prophy Products.

It is also known to incorporate "soft abrasive" polish into dental floss and dental tape, and such products are sold by WhiteHill Manufacturing, Inc. under the trademark Professional Prophy Products.

An oral prophalaxis paste which includes a preselected grade and amount of abrasive material such as pumice, clay or diatimoceous earth is disclosed in U.S. Pat. No. 6,280,707.

It is also known in the art to utilize pumice as an abrasive material for polishing a CRT glass panel wherein the polishing thereof is conducted in the presence of the abrasive material including the pumice in a state of slurry. In polishing CRT glass panels, the polishing pressures are in a range of about 0.2 kg/cm² (200 kg/cm²) to 2.0 kg/cm² (2000 kg/cm$^2$), more preferably in the range of about 0.4 kg/cm$^2$ (400 kg/cm$^2$) to about 1.2 kg/cm$^2$ (1200 kg/cm$^2$). Generally, when the abrasive or polishing force is less than about 0.2 kg/cm$^2$ (200 kg/cm$^2$), the abrasive or polishing force is usually insufficient and the efficiently of the polishing is reduced. Further, it is known to use multiple grades of pumice to affect the polishing process. Typically, a coarse grade pumice is first used in the polishing process to polish the surface of a CRT which is then followed by polishing using a medium grade pumice.

It is also known to use only a single grade of pumice, typically a finer grade, for polishing a CRT surface and to then use a final polishing operation that employs a cerium oxide to obtain the desired polished surface.

Polishes are used to maintain a glossy finish or sheen on surfaces as well as to prolong the useful lives of these surfaces. Appearance enhancement provided by polishes generally results from materials that smooth and clean surfaces through abrasive action, or leave a glossy coating, or both. A description of polishes and uses thereof are set forth at pages 444 through 453 in the Kirk-Othmer Encyclopedia of Chemical Technology, John Wiley & Sons, 1996, 4$^{th}$ Edition, Vol. 19) (the "Chemical Technology, Vol. 19 Reference"). The Chemical Technology, Vol. 19 Reference is incorporated herein by reference.

Many materials have been used as abrasives, usually in one of three forms in polishing operations: grit (loose, granular, or powdered particles); bonded materials (particles are bonded into wheels, segments, or stick shapes); and coated materials (particles are bonded to paper, plastic, cloth, or metal). Grit is often useful for polishing, buffing, lapping, pressure blasting, barrel finishing, jet cutting, and high-pressure jet cutting. Natural abrasives of commercial significance include diamond, corundum, emery, garnet, silica, sandstone, tripoli, pumice, and pumicite, and to a lesser extent, powdered feldspar and staurolite. A description of abrasives and uses thereof are set forth at pages 17 through 37 of the Kirk-Othmer Encyclopedia of Chemical Technology, John Wiley & Sons, 1991, 4th Edition, Vol. 1 (the "Chemical Technology, Vol. 1 Reference"). The Chemical Technology, Vol. 1 Reference is incorporated by reference.

Other known Natural Glasses and Macerals are disclosed and described in Appendix A, Natural Glasses and Macerals, page 540 through 542, in Mineralogy, W. H. Freeman and Company, 2nd Edition (the "Mineralogy Reference"). The Mineralogy Reference is incorporated by reference.

Materials including Thermoplastic materials and thermoset materials generally recognized as "engineering materials", including acrylic polymers, are disclosed and described at pages 371 through 511 of The Handbook of Industrial Materials, Elsevier Advanced Technology, 2nd Edition (the "Industrial Materials Reference"). The Industrial Materials Reference is incorporated by reference herein.

Glasses comprise a wide variety of vitreous amorphous polymers consisting of repeating siloxane (i.e., —(Si—O)—) units in the polymer chain. Some glasses are naturally occurring, such as perlite. Others, such as soda-lime glasses, are produced synthetically. Soda-lime glass is made by melting batches of raw materials containing the oxides of silicon (i.e., $SiO_2$), aluminum (i.e., $Al_2O_3$), calcium (i.e., CaO), sodium (i.e., $Na_2O$), and sometimes potassium (i.e., $K_2O$), or lithium (i.e., $Li_2O$) together in a furnace, and then allowing the melt to cool so as to produce the amorphous product. Glasses may be made in a wide variety of shapes, including sheets or plates, cast shapes, or fibers. Often, glass is not sufficiently smooth as first produced, for the intended end use, and requires further polishing.

Among the glasses requiring polishing for final use include cathode ray tubes and television tubes, eyeglasses, photographic optical components, and laser optical components. These glasses are prepared in a wide array of chemical compositions, and thus have various hardnesses and physical properties. Being a natural glass itself, the unexpanded perlite ore polishing composition is useful for polishing glasses, provided the glass is equal to or less than the hardness of the unexpanded perlite ore polishing composition.

It is also known in the art to etch or polishing a surface of an article using a method and apparatus for blowing an airstream containing use submicron particles thereacross. One example of a surface process method by blowing submicron particles is disclosed in U.S. Pat. No. 5,928,719.

Principles of grinding and polishing of materials, such as plastics and polymers, including the use of grinding, hand polishing and automated polishing systems are described in Pages 1 through 10 of the STANDARD GUIDE FOR PREPARATION OF PLASTICS AND POLYMERIC SPECIMENS FOR MICROSTRUCTURAL EXAMINATION, Designation: E 2015-99, American Society for Testing and Materials (the "ASTM Standard Guide Reference"). The ATSM Standard Guide Reference in Section 11 captioned "Polishing" sets forth information relating to rough polishing and fine or final polishing. ATSM Standard Guide Reference includes methods for measuring flatness of a polished surface, typical applied pressures to obtain the desired polishing and effective wheel speeds for automated polishing. The disclosures set forth in the ATSM Standard Guide Reference can be used in practicing this invention.

The rate at which the final polishing of a surface can be obtained using the unexpanded perlite ore composition of the present invention can be by microscopical analysis by reflected light.

For example, if the selected distribution of selected sizes of the grains of unexpanded perlite ore composition have a ($d_{90}$) having a larger particle size, e.g. greater than 245 μm, then the rate at which the unexpanded perlite ore composition comminutes or fractures will be higher which is desirable for a higher level of coarse polishing. On the other hand, if the selected distribution of selected sizes of the grains of unexpanded perlite ore composition have a ($d_{90}$) having a smaller particle size, e.g. about 100 μm, then the rate at which the unexpanded perlite ore composition comminutes or fractures will lower which is desirable for a fine polish level.

It is envisioned that measurements of rates of effective coarse polishing and fine polishing can be determined by microscopical analysis of a polished surface using reflected light in a manner similar to the method described in Pages 1 through 4 of the STANDARD PRACTICE GUIDE FOR PREPARING COAL SAMPLES FOR MICROSCOPICAL ANALYSIS BY REFLECTED LIGHT, Designation: D2797-85 Reapproved 1999), American Society for Testing and Materials (the "ASTM Microscopical Analysis Reference"). The ATSM Microscopical Analysis Reference in Section 9 captioned "Preparation of Briquet Surface" sets forth information relating to grinding and polishing of a briquet on a lap to obtain a surface suitable for microscopic examination. The same method can be used to determine the effectiveness of both coarse polishing and fine polishing of a desired surface.

The disclosure of all of the above references and Patents and other references referred into this specification are hereby incorporated by reference as if set forth verbatim herein.

BRIEF SUMMARY OF THE INVENTION

The present invention discloses a new, novel and unique unexpanded perlite ore polishing composition which, through continued fracturing of grains of unexpanded perlite ore having a selected distribution of particle sizes during polishing under an abrasive force, develops a sufficiently low level of abrasiveness making it suitable for use in polishing. The unexpanded perlite ore polishing composition yields a final polishing composition which is capable of achieving a high gloss finish on polymers, including acrylic polymers and dentures under an abrasive force and glass compositions.

The unexpanded perlite ore polishing composition includes a base unexpanded perlite ore material having grains of an unexpanded perlite ore of a selected distribution of particle size which undergo fracturing of the grains as a function of the polishing force applied to the base unexpanded perlite ore material. The selected distribution of particle size of the grains of unexpanded perlite ore have particle sizes of less than about 245 µm. The base unexpanded perlite ore material is responsive to an abrasive force, such as a manually applied physical force or a pressurized gas stream being applied to the base unexpanded perlite ore material during polishing. During the application of an appropriate abrasive force, the grains of unexpanded perlite ore exhibit continued fracturing to yield a final polishing composition having particle sizes of less than about 100 µm. The final polishing composition has a sufficiently low level of abrasiveness making it suitable for use in polishing.

In its broadest aspect, the invention resides in an unexpanded perlite ore polishing composition having a single base material. The single base material comprises grains of unexpanded perlite ore having a selected distribution of particle sizes that range in particle size from about 5 µm to about 352 µm and the selected distribution at about 50% by volume of grains of unexpanded perlite ore have a particle size in the range of about 20 µm to about 120 µm.

The base unexpanded perlite ore material is responsive to a force being applied to the base material during polishing resulting in continued fracturing of the grains of unexpanded perlite ore. This yields a final polishing composition with grains of unexpanded perlite ore having a distribution of particle sizes with a greater number of grains of unexpanded perlite ore having a smaller particle size than the number of grains of unexpanded perlite ore having a smaller particle size than the selected distribution of the base material prior to application of the abrasive force.

None of the known prior art, anticipates, discloses, teaches or suggest a unexpanded perlite ore polishing composition having as base material or base composition having grains of an unexpanded perlite ore material. Nor does the known prior art, anticipates, discloses, teaches or suggest a base material or base composition having grains of an unexpanded perlite ore of a selected particle size has an abrasive force applied to the unexpanded perlite ore material that yields a final polishing composition with or having a sufficiently low level of abrasiveness for making it suitable for use in polishing.

This invention is clearly new, novel and unobvious to persons skilled-in-the-art for all the reasons set forth herein.

Therefore, one advantage of the unexpanded perlite ore polishing composition of the present invention is that the base unexpanded perlite ore material having grains of an unexpanded perlite ore having a selected distribution of particle size undergoes continued fracturing of the grains as a function of the abrasive force, e.g., a polishing force, applied to the unexpanded perlite ore material yielding a final polishing composition having a sufficiently low level of abrasiveness making it suitable for use in polishing.

Another advantage of the present invention is that the final polishing composition, which is still in the form of an unexpanded perlite ore, has a distribution of particle sizes having a greater number of smaller grains of unexpanded perlite ore than the number of smaller grains of unexpanded perlite ore having in the selected distribution of the base material prior to application of an abrasion force.

Another advantage of the present invention is that the base unexpanded perlite ore polishing composition has a ($d_{90}$) particle size of grains of unexpanded perlite ore in the range of about 80 µm to about 245 µm.

Another advantage of the present invention is that the final polishing composition has a distribution of particle size in the range of about 20 µm to about 100 µm with a preferred particle size in the range of about 20 µm to about 50 µm.

Another advantage of the present invention is that the base material includes grains of unexpanded perlite ore having a selected distribution of particle sizes which range in particle size from about 10 µm to about 245 µm. The selected distribution has at least 50% by volume of grains of unexpanded perlite ore having a particle size of about 20 µm to about 120 µm.

Another advantage of the present invention is that the unexpanded perlite ore polishing composition can be used as an unexpanded perlite ore composition for a polishing polymers and acrylic polymers.

Another advantage of the present invention is that the unexpanded perlite ore polishing composition can comprise a base composition comprising a first base unexpanded perlite ore material having grains of unexpanded perlite ore of a first selected distribution of particle size and a second base unexpanded perlite ore material having grains an unexpanded perlite ore of a second selected distribution of particle size, both of which are responsive to a abrasive force to yield a final polishing composition with a distribution of particle size of less than 50 µm and wherein the final polishing composition has a sufficiently low level of abrasiveness making it suitable for use in polishing.

Another advantage of the present invention is that the unexpanded perlite ore polishing composition base material and/or base composition can include a carrier selected from the group consisting of liquids, gases and mixtures thereof.

Another advantage of the present invention is that a method for polishing a surface of an article comprising applying a quantity of unexpanded perlite ore polishing composition comprising a base unexpanded perlite ore material having grains of an unexpanded perlite ore of a selected distribution of particle size and applying an abrasive force to the unexpanded perlite ore base material and fracturing the grains of unexpanded perlite ore to yield a final polishing composition having a sufficiently low level of abrasiveness making it suitable for polishing the surface of an article.

Another advantage of the present invention is that the method of preparing the unexpanded perlite ore polishing composition base material and/or base composition does not require use of the expansive phase as is required for "expanded perlite" products. This is a significant advantage in that the expansion process is a relatively expensive process.

Another advantage of the present invention is that the unexpanded perlite ore polishing composition can use in a device for directing a unexpanded perlite ore polishing composition under an abrasive force, e.g., a gas stream under pressure, against a surface of a work piece and polishing the same. An auxiliary polishing force by being applied to the surface by a separate member, e.g., a rotating driven member.

Another advantage of the present invention is that a method of preparing an unexpanded perlite ore polishing composition is shown.

Another advantage of the present invention is that the method of preparing the unexpanded perlite ore polishing composition base material and/or base composition does not require us of the expansive phase as is required for "expanded perlite" products. This is a significant advantage in that the expansion process is a relatively expensive process.

Another advantage of the present invention is that the unexpanded perlite ore polishing composition base material and/or base composition has a density significantly higher than the density of "expanded perlite", and as such, the unexpanded perlite ore is less likely to dust.

Another advantage of the present invention is that several methods of using the unexpanded perlite ore polishing composition are shown.

Another advantage of the present invention is that the unexpanded perlite ore polishing composition has utility for use in a dental prophalaxis paste.

Another advantage of the present invention is that the unexpanded perlite ore polishing composition has utility for use in a strip material for polishing teeth. The strip material may comprise a strip member comprising a material configured for use as dental floss or for use as dental tape.

Another advantage of the present invention is that acrylic denture polishing compositions and CRT glass surface polishing compositions have safety advantages in that the compositions have a concentration of crystalline silica of less than 0.1%.

BRIEF DESCRIPTION OF THE DRAWING

The present invention will become more fully understood from the following detailed description of a preferred, but non-limiting, embodiment thereof described in connection with the accompanying drawings wherein.

DETAILED DESCRIPTION OF THE INVENTION

Background

Figure 1:
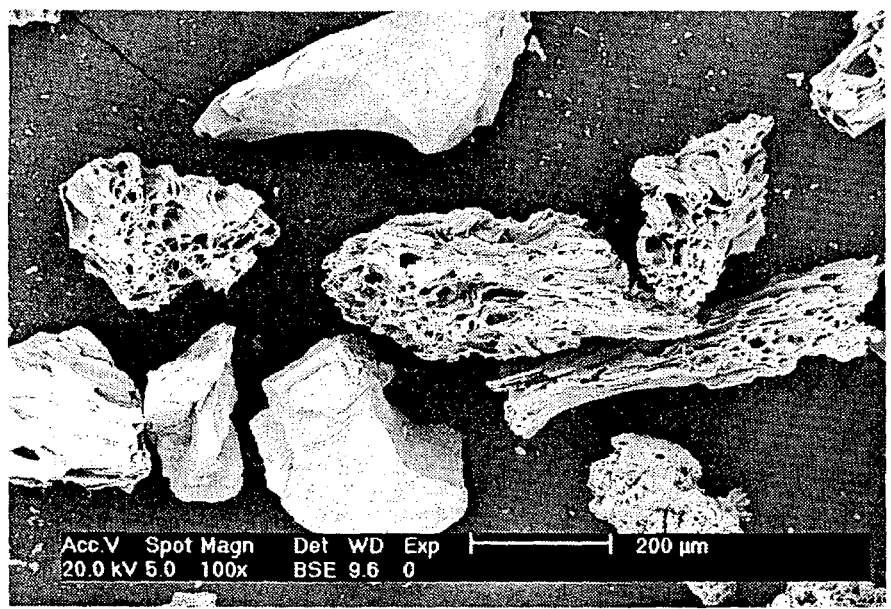
FIG. 1 is a scanning electron micrograph of grains of pumice magnified 100×.

The unexpanded perlite ore polishing composition is made from a natural glass, of which unexpanded perlite ore is the predominating form of natural glass. The term "natural glass" is used here in the conventional sense and refers to natural glasses, commonly referred to as volcanic glasses, which are formed by the rapid cooling of siliceous magma or lava. Most natural glasses are chemically equivalent to rhyolite. Natural glasses which are chemically equivalent to trachyte, dacite, andesite, latite, and basalt are known but are less common. The term "obsidian" is generally applied to dark, most often black, massive natural glasses that are rich in silica (i.e., $SiO_2$). Obsidian glasses may be classified into subcategories according to their silica content, with rhyolitic obsidians (containing typically about 73% $SiO_2$ by weight) as the most common.

Unexpanded perlite is a hydrated natural glass containing typically about 72-75% $SiO_2$, 12-14% $Al_2O_3$, 0.5-2% $Fe_2O_3$, 3-5% $Na_2O$, 4-5% $K_2O$, 0.4-1.5% CaO (by weight), and small concentrations of other metallic elements. Perlite is distinguished from other natural glasses by a higher content (2 to 10% by weight) of chemically bonded water, the presence of a vitreous, pearly luster, and commonly, but not always, a characteristic concentric or arcuate onion skin-like (i.e., perlitic) fractures. This kind of perlite is sometimes referred to as unexploded perlite, unexpanded perlite, raw perlite or perlite ore.

Since unexpanded perlite is a rhyolitic vitreous rock of volcanic origin, the composition according to elemental analysis will vary due to different origin. For example, for some unexpanded perlite, the $SiO_2$ may range from 72.1% to 74.2% and the $Al_2O_3$ may range from 12.3% to 13.5%.

This invention is not limited to any specific perlite composition according to an elemental analysis of unexpanded perlite. It is envisioned that all compositions of unexpanded perlite, sometimes referred to herein as unexpanded perlite ore, can be used in practicing this invention.

It is important to distinguish that the teachings of the present invention resides in the use of unexpanded perlite ore having high density which is on the order of about 65 lbs. per cubic foot to about 70 lbs. per cubic foot. This is distinguished from expanded perlite which has a low density on the order of about 5 lbs. per cubic foot to about 20 lbs. per cubic foot. Expanded perlite is derived from unexpanded perlite ore, or perlite ore, known as a mineral, and is fabricated by heating the unexpanded perlite ore to temperature in the order of 900° C. to 1000° C.

As a result of the immediate heat applied to the perlite ore, the water of hydration within the unexpanded perlite is transformed into a gas phase beginning at about 800° C., and the melted particles expand to a multiple of the initial volume.

The examples discussed herein provide specific examples of a base material or base composition wherein the grains of unexpanded perlite ore have a selected distribution of particle sizes wherein the ($d_{90}$) is in the range of about 60 µm to about 245 µm.

Fracture characteristics of abrasive materials are important to polishing performance, as well as the resulting grain shapes and microstructural features. This is referred to as perlitic mode of fracture. The perlitic mode of fracture is exceptionally well suited for use in an expanded perlite ore polishing composition for polishing a surface, such as for example an acrylic polymer surface used in fabrication dentifrice. The polishing function is dependent on a final polishing composition having grains of fractured, unexpanded perlite ore in small particle sizes formed by an abrasive force being applied to the unexpanded perlite ore polishing composition.

Thus, this invention resides in use of unexpanded perlite ore and the term "unexpanded perlite ore" is used herein to distinguish the same from expanded perlite. As discussed above, the term "expanded perlite" is used in the art to identify material derived from unexpanded perlite ore, or perlite ore, by heating the unexpanded perlite ore as described above.

In essence, unexpanded perlite ore has significant structural and physical characteristics relative to those of expanded perlite which is the composition generally used as described in the prior art.

Figure 2:
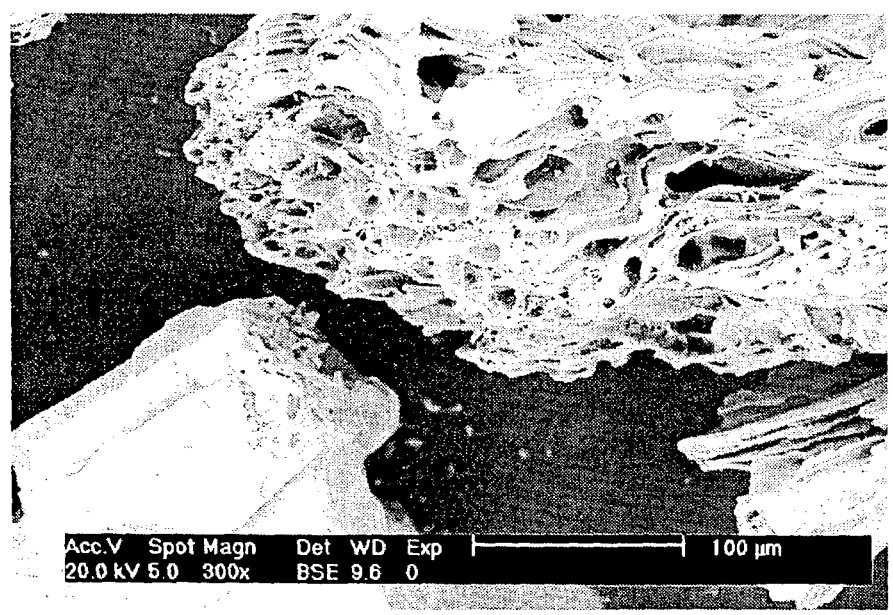
FIG. 2 is a scanning electron micrograph of grains of pumice magnified 300×.

As noted above, FIGS. 1 and 2 are prior art micrographs images that disclose the grain structure of pumice which, during polishing, results in the scratching of the surface being polished. Pumice has a high granular compressive strength (>22N/mm² or 220 kg/cm²).

Typically, pumice is used for coarse polishing of a surface when it is desired to rapidly remove a large quantity of material. An example of such an application is for the initial abrasion polishing performed on a glass CRT tube surface.

Typically, a fine polish is then used on the CRT tube surface after use of the coarse pumice abrasive to remove the scratches and to obtain the desired finish polish on a surface. Use of an unexpanded perlite ore polishing composition of the present invention eliminates the creation of scratches and eliminate the necessity for a first coarse abrasive process step.

Figure 3:
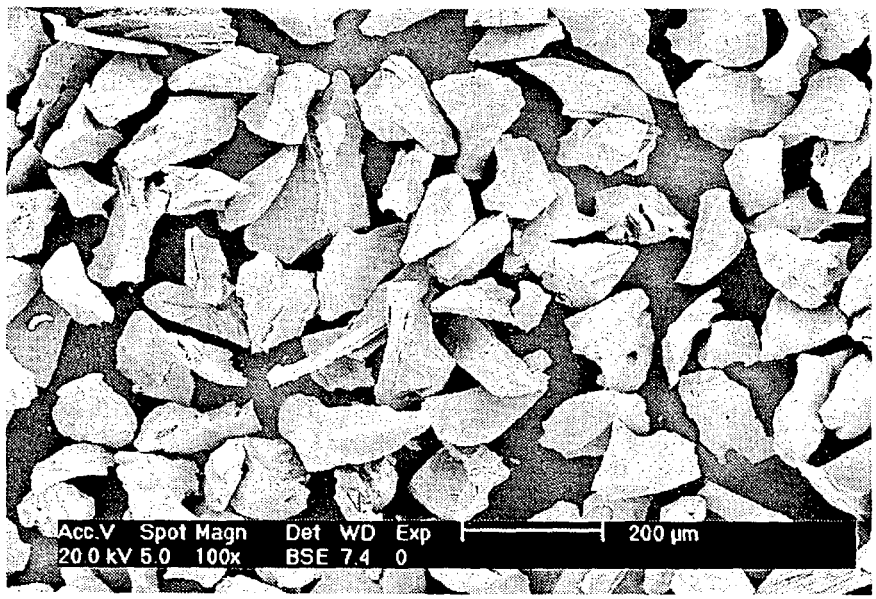
FIG. 3 is a scanning electron micrograph of grains of unexpanded perlite ore magnified 100×.
Figure 4:
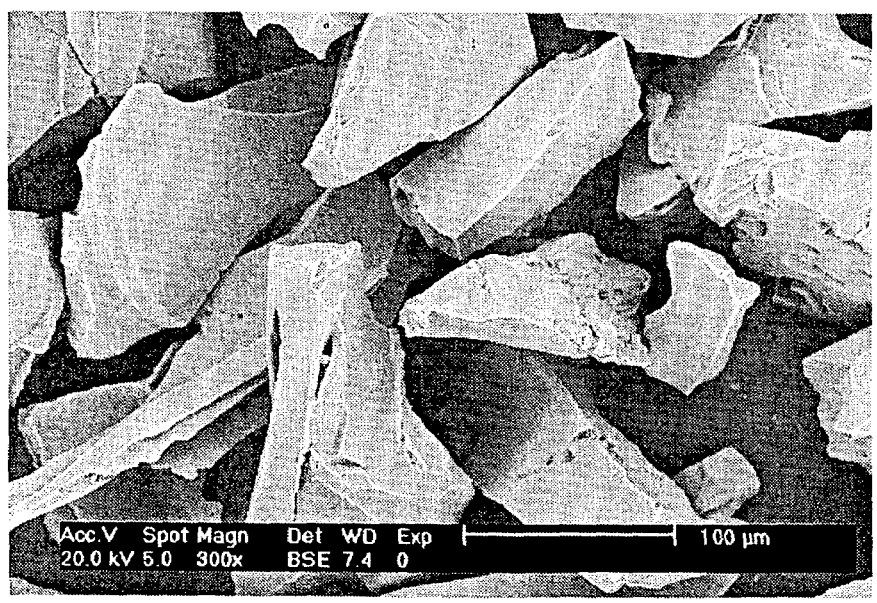
FIG. 4 is a scanning electron micrograph of grains of unexpanded perlite ore magnified 300×.

FIGS. 3 and 4 comprise scanning electron micrograph images that disclose the grain structure of unexpanded perlite ore has a smoother exterior surface, as compared to pumice. The structure of the grains of unexpanded perlite ore lend themselves to continued fracturing. That is, the application of an abrasive force, e.g., a polishing force, e.g., a pressurized gas stream, onto a grain of unexpanded perlite ore will cause that grain to fracture into a grain of smaller particle size which is highly desirable. Of course, grains of larger particle size exhibit a higher degree of fracture or of fracturing.

As a result, the interaction between the exterior surface of the grain of unexpanded perlite ore having a relatively smooth exterior surface reacts or co-acts with the surface being polished through friction developed by an abrasive force to yield a fine polishing composition.

Figure 5:
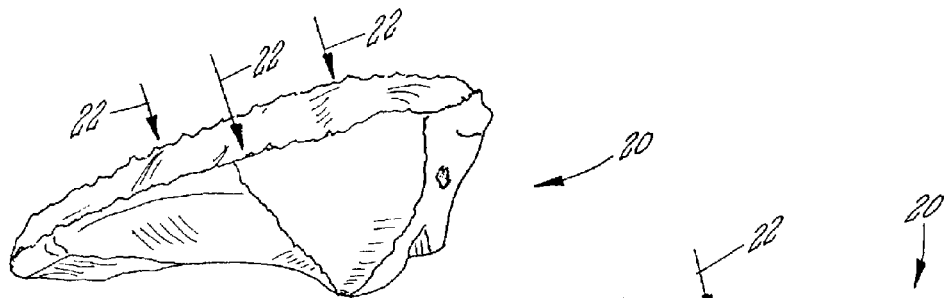
FIG. 5 is a pictorial representation of a typical grain of unexpanded perlite ore having a particle size as shown in FIG. 4 being subjected to an abrasive force.

FIG. 5 depicts the mechanical process of fracturing of a grain of unexpanded perlite ore shown as 20 having a larger particle size, e.g. 125 µm. The application of an abrasive force to the grain of unexpanded perlite ore 20 is illustrated by arrows 22.

Figure 6:
FIG. 6 is a pictorial representation of the grain of unexpanded perlite ore shown in FIG. 5 fracturing under an abrasive force into smaller grains of unexpanded perlite ore.

FIG. 6 depicts that the application of the abrasive forces 22 cause continued fracturing or comminution of the grains of unexpanded perlite ore, initially having a larger particle size, into smaller grains of unexpanded perlite ore depicted by fracture sections depicted by 30 and 32. Thereafter, fracture sections of grains depicted by 30 and 32 then respond to the abrasive forces 22 to further fractionize or break into smaller grains of unexpanded perlite ore.

Figure 7:
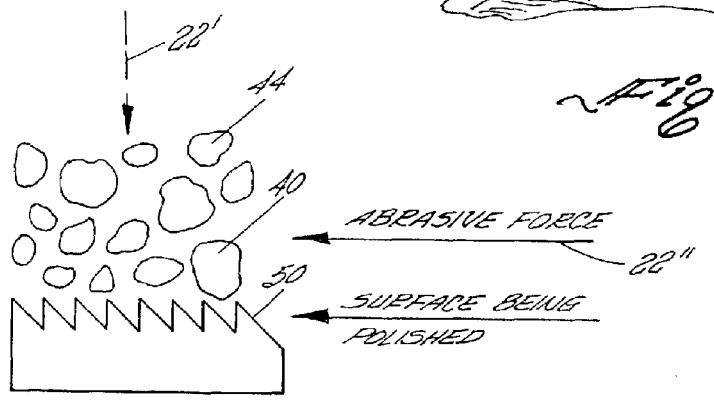
FIG. 7 is a pictorial representation of an unexpanded perlite ore polishing composition using the teachings of this invention positioned relative to a surface of a work piece to be polished at the commencement of a polishing process.
Figure 8:
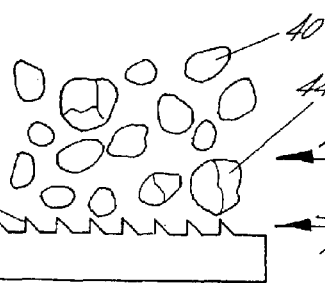
FIG. 8 is a pictorial representation of a unexpanded perlite ore polishing composition illustrating the continued fracturing of the grains of larger particle sizes of unexpanded perlite ore having a larger particle size which results in a final polishing composition of grains of unexpanded perlite ore having a smaller particle size.
Figure 9:
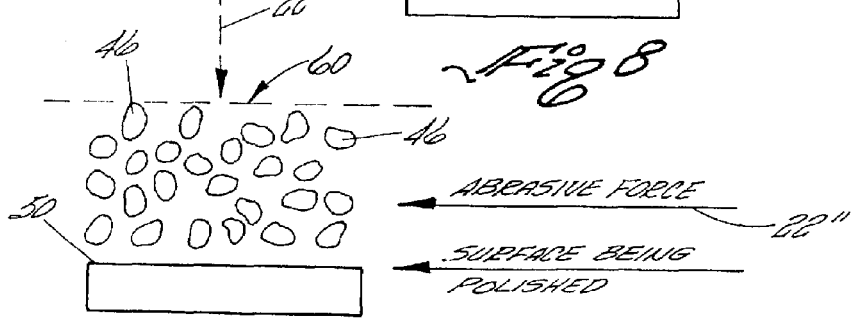
FIG. 9 is a pictorial representation of an unexpanded perlite ore polishing composition showing the final polishing composition of the unexpanded perlite ore after continued fracturing in response to an abrasive force for providing a polished surface.

FIGS. 7, 8 and 9 illustrate that the continued application of the abrasive forces 22 continue to result in the fracturing or comminution of the grains of unexpanded perlite ore, having a larger particle size of which the grains depicted in 40 is typical. Subsequently, they yield the fine polishing composition comprising grains of unexpanded perlite ore, of which grains depicted as 44 are typical, which continue to exhibit continued fracturing in response to the abrasive forces 22 resulting in or yielding grains of unexpanded perlite ore 46 which are suitable for polishing a surface 50 of an article.

In FIG. 7, the abrasive force 20 may be applied in a direction depicted by dashed arrow 22' or as a polishing force shown by arrow 22". In FIG. 7, the surface 50 is depicted pictorially as having a large sawtooth surface.

In FIG. 8, surface 50 is depicted as having a reduced sawtooth surface showing that the polishing action is effective. FIG. 9 depicts surface 50 as being polished. The final polishing composition shown in FIG. 9 has a larger number of small grains 46.

The unexpanded perlite composition may be incorporated in or used as a polishing element in a dental prophalaxis paste, or in dental floss or dental tape. For example, the paste element in a dental prophalaxis paste or the strip member in dental floss or dental tape is depicted by dashed line 60 in FIG. 9.

Figure 10:
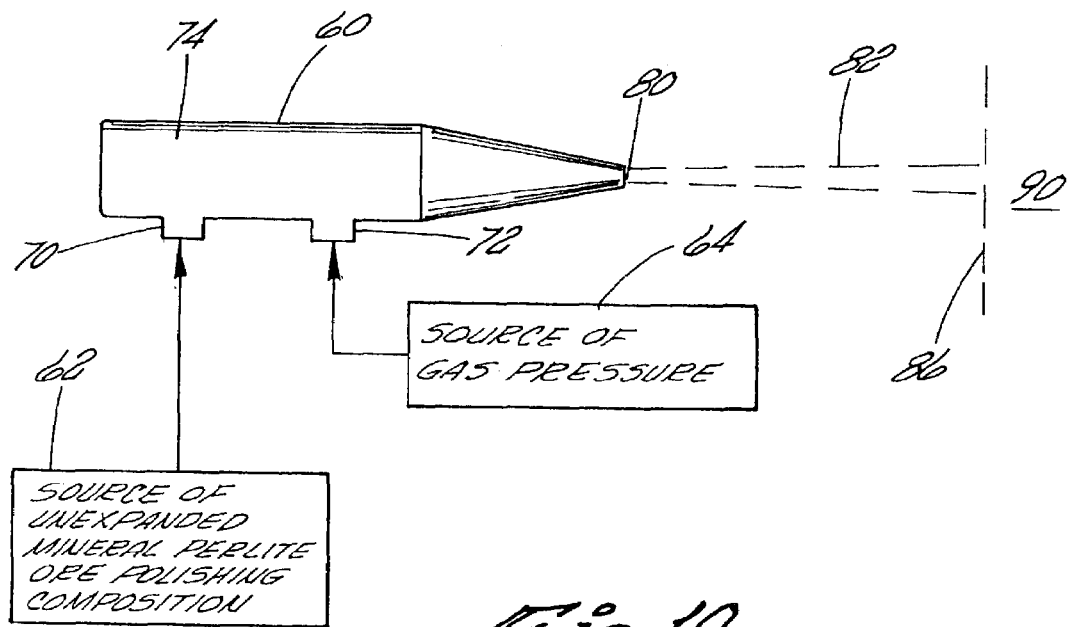
FIG. 10 is a pictorial representation of a microblasting nozzle for use with a source of unexpanded perlite ore polishing composition of the present invention and a source of gas pressure as an abrasive force for polishing articles.

In FIG. 10, the pictorial representation of a microblasting nozzle 60 is used with a source of unexpanded perlite ore polishing composition of the present invention, generally shown as 62, and a source of gas pressure, generally shown as arrow 64.

The nozzle 62 has a first input 70 and a second input 72. First input 70 is operatively coupled to a source of unexpanded perlite ore polishing composition 62 to enable the nozzle 60 to draw grains of unexpanded perlite ore from the source 60 into the chamber 74. The source of gas pressure 64 is to apply to the second input 72 and the gas pressure within chamber 74 develops a differential pressure between the pressure of the gas and atmosphere to draw the grains of unexpanded perlite ore into the chamber 74.

In chamber 74, the grains of unexpanded perlite ore composition are mixed with the gas and are directed out of the nozzle 60, under the pressure of the gas stream, through the nozzle orifice 80. A narrow, pressurized particle stream depicted by dash line 82 is emitted from or directed through the orifice 80. The size, width and pattern of the pressurized particle stream 82 is determined by the nozzle orifice size and shape, the particle sizes of the grains of unexpanded perlite ore and the pressure of the gas stream which functioned as the abrasive force.

The pressurized particle stream 82 comprises both the unexpanded perlite ore polishing composition and a gas stream which functions as an abrasive force, both of which are directed onto a surface 86 of a work piece 90 to polish the surface 86.

In this application, it is desirable that the hardness of the grains of unexpanded perlite ore forming the unexpanded perlite ore polishing compositions generally have a hardness of approximately equal to the hardness of glass beads. The use of glass beads and the characteristics of thereof including hardness are known to persons skilled in the art.

The use of the microblasting device described above with respect to FIG. 10 has applications for treating the surfaces of materials used primarily in the aerospace and medical fields. In the aerospace field, the unexpanded perlite ore polishing composition may be used for polishing of aluminum aircraft parts. In the medical field, the unexpanded perlite ore polishing composition may be used for treating stainless steel medical devices, i.e., reamers and drivers.

In typical applications, air is used as the gas and air pressures may vary from 40 psi to about 150 psi. The actual pressure is determined by the particle size of the unexpanded perlite ore and the width of the pressurized particle stream.

Smaller areas to be treated by using the microblasting assembly described in FIG. 10 will be treated with air pressures of about 60 psi using a nozzle having a diameter of about 0.25 inches which is of sufficient size to pass a pressurized particle stream using the unexpanded perlite ore polishing compositions disclosed herein.

It is envisioned that larger surfaces would use higher air pressure than 60 psi and nozzle orifices having a diameter greater than 0.25 inches.

A composition of unexpanded perlite ore using the teachings of the present invention has utility as a microblasting agent in that such a composition, particularly a fine unexpanded perlite ore composition, may be used in lieu of or in combination with aluminum oxide. Aluminum oxide is presently used as a microblasting agent for etching of aluminum and stainless steel. Also, it is envisioned that the unexpanded perlite ore composition could be used in lieu of or in combination with glass beads used as a microblasting agent.

Figure 11:
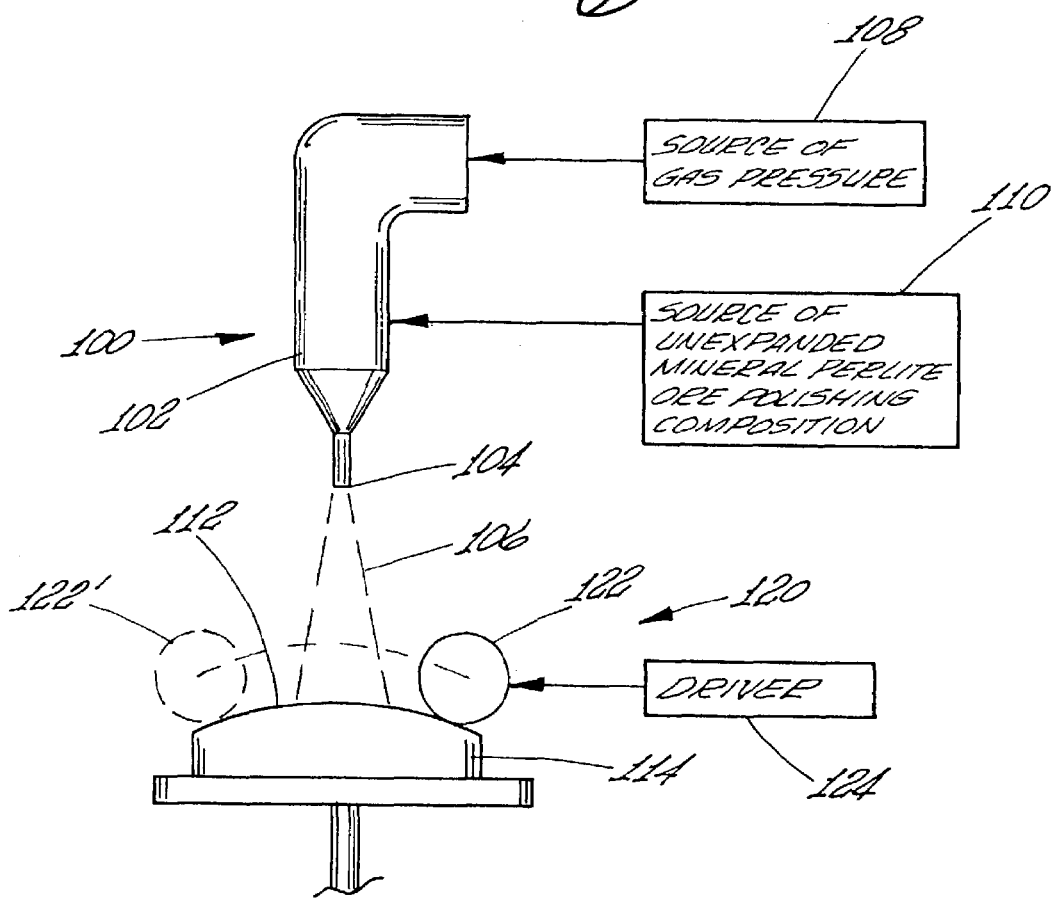
FIG. 11 is a pictorial representation of a nozzle assembly having a nozzle for forming a wide distribution pattern for directing a continuous flow of unexpanded perlite ore polishing composition onto a surface of a optical glass being polished by a rotatable moveable driven polishing member.

FIG. 11 is a pictorial representation of a nozzle having a wide distribution pattern for applying a continuous flow of unexpanded perlite ore polishing composition onto a surface of an optical glass being polished by a moveable polishing member.

In FIG. 11, the pictorial representation of a nozzle assembly is shown generally by arrow 100. A source of gas pressure 108 and a source of an unexpanded perlite ore polishing composition 110, using the teachings of this invention, are applied as and used as inputs to the nozzle assembly 100.

The nozzle assembly 100 includes a nozzle 102 having an orifice 104 having a wide continuous pressure distribution pattern identified as by dash lines 106. The nozzle 102 applies a continuous flow of pressurized stream of unexpanded perlite ore polishing composition onto a surface 112 of a optical glasswork piece 114. The surface 112 is simultaneously being polished by rotating, movable polishing member shown generally as 120.

The nozzle 104 generates the spray pattern, shown by dash lines 106, comprising a stream of unexpanded perlite ore polishing composition, under appropriate pressure, which is directed on to the surface 112 to be polished. In this example, the surface 112 is located on a CRT glass tube 114.

The polishing member 120 is a rotating polishing member 122 driven by a drive member 124 across the surface 112. The drive rotating member 122 contacts and applies a polishing force on the unexpanded perlite ore polishing composition which is directed on to the surface 112 by the spray pattern 106. The unexpanded perlite ore polishing composition reacts with the surface 112 as a result of abrasive forces generated by both the actions of the: (i) continuous spray pattern 106, under the appropriate gas pressure and volume as a polishing force; and (ii) the polishing force applied by the driven polishing member 122 resulting in the surface 112 being polished to a highly polished surface.

Many polymers have surfaces that require polishing to obtain a high gloss. The term "polymers" as used herein includes thermoplastic and thermoset materials. Thermoplastic materials are those which soften under the action of heat and harden again to their original characteristics on cooling, that is, the heating-cooling cycle is fully reversible. By conventional definition, thermoplastics are straight and branched linear chain organic polymers with a molecular bond. Examples of well-known thermoplastics include products of acrylonitrile butadiene styrene (ABS), styrene acrylonitrile (SAN), acrylate styrene acrylonitrile (ASA), and methacrylate butadiene styrene (MBS). Also included are polymers of formaldehyde, known as acetals; polymers of methyl methacrylate, known as acrylic plastics; polymers of monomeric styrene, known as polystyrenes; polymers of fluorinated monomers, known as fluorocarbons; polymers of amide chains, known as nylons; polymers of paraffins and olefins, known as polyethylenes, polypropylenes, and polyolefins; polymers composed of repeating bisphenol and carbonate groups, known as polycarbonates; polymers of terephthalates, known as polyesters; polymers of bisphenol and dicarboxylic acids, known as polyarylates; and polymers of vinyl chlorides, known as polyvinyl chlorides (PVC). High performance thermoplastics have extraordinary properties, for example, polyphenylene sulfide (PPS), which has exceptionally high strength and rigidity; polyether ketone (PEK), polyether ether ketone (PEEK), polyamide imide (PAI), which have very high strength and rigidity, as well as exceptional heat resistance; and polyetherimide (PEI), which has inherent flame resistance. Unusual thermoplastics include ionomers, i.e., copolymers of ethylene and methacrylic acid that have ionic rather than covalent crosslinking which results in behavior resembling that of thermoset plastics in their operating range; polyvinylcarbazole, which has unique electrical properties; and polymers of isobutylene, known as polyisobutylenes, which are viscous at room temperature.

Thermoset plastics are synthetic resins that are permanently changed upon thermal curing, that is, they solidify into an infusible state so that they do not soften and become plastic again upon subsequent heating. However, certain thermoset plastics may exhibit thermoplastic behavior over a limited portion of their useful application ranges, and are similarly useful as matrix components of the present invention. Some types of thermoset plastics, especially certain polyesters and epoxides, are capable of cold curing at room temperature. Thermoset plastics include alkyds, phenolics, epoxides, aminos (including urea-formaldehyde and melamine-formaldehyde), polyimides, and some silicon plastics.

The properties and applications of thermoplastics and thermoset plastics are disclosed and described in greater detail in the Industrial Materials Reference. Of all the polymers aforementioned, acrylic polymers are most useful for dentures, an application for which the unexpanded perlite ore polishing composition is particularly well suited.

Unexpanded Perlite Ore Polishing Composition

The unexpanded perlite ore polishing composition utilizes, in one embodiment, a base material having grains of unexpanded perlite ore. The particle size distribution of the unexpanded perlite ore used in the base unexpanded perlite ore is selected to be within a prescribed or selected distribution range for the unexpanded perlite ore polishing composition to obtain the desired speed of polishing and surface gloss. The particle size distribution of the unexpanded perlite ore polishing composition is best determined in accordance with the phenomenon of scattered light from a laser beam projected through a stream of particles. The amount and direction of light scattered by the particles is measured by an optical detector array and then analyzed by a microcomputer which calculates the size distribution of the particles in the sample stream. Data reported may be collected on a Leeds and Northrup Microtrac X100 laser particle size analyzer (Leeds and Northrup, North Wales, Pa.). This instrument can determine particle size distribution over a particle size range from about 0.12 microns to about 704 microns.

In this description, the distribution of particle size in unexpanded perlite ore is designated on the bottom particle size ($d_{10}$), the median particle size ($d_{50}$) and top particle size ($d_{90}$) being defined as that size for which 10 percent, 50 percent, or 90 percent of the volume is smaller than the indicated size, respectively. The examples discusses herein provide specific examples of a base material or base composition wherein the grains of unexpanded perlite ore have a selected distributed of particle sizes wherein the ($d_{90}$) is in the range of about 60 µm to about 162 µm.

It is envisioned that the following selected distribution of particle size can be used in the unexpanded perlite ore polishing composition of the present invention.

| | Range of Particle Size (µm) | Range of Particle Size at ($d_{90}$) Volume (µm) | Range of Particle Size at ($d_{50}$) Volume (µm) |
|---|---|---|---|
| Base Material (Prior to screening) | 1.0 to 1000 | 80 to 244 | 20 to 100 |
| Base Material* (After Screening) | 12 to 244 | Approximately 94 | Approximately 55 |
| First Base** Unexpanded perlite ore Material | 12 to 352 | 140 to 160 | 60 to 80 |
| Second Base*** Unexpanded perlite ore Material | 1.2 to 296 | 60 to 90 | 20 to 30 |
| Base Composition (Blend of first base unexpanded perlite ore material and second base unexpanded perlite ore material at a 50:50 Ratio) | 1.3 to 352 | 110 to 130 | 30 to 50 |

*Harborlite Perlite Grade PA-1000 (See Example 1) using a 200-mesh sieve, with the material passing through the sieve retained
**Harborlite Perlite Grade PA-1000 (See Example 1) using a 100-mesh sieve, with the material passing through the sieve retained
***Harborlite Perlite Grade PA-4000 (See Example 2) using a 100-mesh sieve, with the material passing through the sieve retained A method of making unexpanded perlite ore polishing composition includes the step of first preparing, from a crushed and milled unexpanded perlite ore, a base material which provides grains of unexpanded perlite ore having the desired distribution of particle sizes.

The so formed unexpanded perlite ore composition is applied to a surface to be polished, e.g. dentures, and an appropriate polishing force is applied top the unexpanded perlite ore polishing composition, e.g. for polishing acrylic polymer dentures, is applied in an appropriate motion, e.g., for polishing an acrylic polymer, a polishing motion in the form of a buffing wheel against the acrylic polymer surface being polished.

Final Polishing of Surface

Formal quantitation of the shininess of a surface, such as, glossy polymer surfaces, is rare. Typically, a visual judgment of appearance is usually sufficient for many applications.

However, one useful method of quantitatively determining the degree of polishing is by measurement of sheen. For example, the sheen of a polymer may be measured by determining the 85° sheen, sometimes referred to as specular gloss, of the polymer. A calibrated Glossgard® II 85° glossmeter (Pacific Scientific, Silver Springs, Md.) may be placed over a polished surface. A reading obtained directly from the instrument. If the reading is greater than the 85° Sheen, the reading indicates that the surface is glossier than an 85% sheen.

EXAMPLES

The following are examples of unexpanded perlite ore polishing compositions using the teachings of the present invention.

Example 1

The following example utilizes Harborlite Perlite Grade PA-1000 and the specifications thereof is as follows:

| | |
|---|---|
| PRODUCT: | HARBORLITE PERLITE |
| GRADE: | PA-1000 |
| COMPOSITION: | Perlite, amorphous alumina silicate. |
| DENSITY: | 65.0-70.0 lbs. per cubic foot (bulk density). |
| BULK SPECIFIC GRAVITY: | 1.43 g/ml |
| pH: | 7.6 |
| SURFACE | <0.3 |

-continued

| MOISTURE: | | | |
|---|---|---|---|
| DRY SCREEN | | −100 | |
| ANALYSIS | 100 | 200 | −200 |
| TYPICAL RANGE: | 0.0-8.0 | 20.0-47.0 | 50.0-75.0 |
| (% Retained) | | | |
| CHEMICAL | 72.0% SiO2; 13.0% Al2O3; 4.5% Na2O; .7% CaO; | | |
| ANALYSIS: | .7% Fe2O3; 5.0% K2O; 1% TiO2; <.1% MgO; | | |
| | <.1% SO3; .1% MnO2; 1.1 H2O; 2.8 LOI. | | |

Harborlite® PA 1000 (Harborlite Corporation, Santa Barbara, Calif.) was screened through a 100-mesh sieve, with the material passing through the sieve retained. A particle size distribution of $d_{10}=31.4$ μm, $d_{50}=70$ μm, and $d_{90}=128$ μm was obtained for this product. This product is particularly well suited to coarse polishing of highly irregular surfaces. An example of such surfaces are the surfaces of molded or cast part using "engineering materials" set forth in the Industrial Materials Reference. This composition can also be used in a prophy paste.

Example 2

The following example utilizes Harborlite Perlite Grade PA-4000 and the specifications thereof is as follows:

| PRODUCT: | HARBORLITE PERLITE | | | |
|---|---|---|---|---|
| GRADE: | PA 4000 | | | |
| COMPOSITION: | Perlite, amorphous alumina silicate. | | | |
| DENSITY: | 65.0-70.0 lbs. per cubic foot (bulk density). | | | |
| BULK SPECIFIC | 1.43 g/ml | | | |
| GRAVITY: | | | | |
| pH: | 7.6 | | | |
| SURFACE | <0.3 | | | |
| MOISTURE: | | | | |
| DRY SCREEN | PLUS | −200 | −325 MINUS | MINUS |
| ANALYSIS | 200 | 325 | 400 | 400 |
| TYPICAL RANGE: | 10.0 | 8.4 | 4.4 | 77.2 |
| (% Retained) | | | | |
| CHEMICAL | 72.0% SiO2; 13.0% Al2O3; 4.5% Na2O; .7% CaO; | | | |
| ANALYSIS: | .7% Fe2O3; 5.0% K2O; .1% TiO2; <.1% MgO; | | | |
| | <.1% SO3; .1% MnO2; 1.1 H2O; 2.8 LOI. | | | |

Harborlite® PA 4000 (Harborlite Corporation, Santa Barbara, Calif.) was screened through a 100-mesh sieve, with the material passing through the sieve retained. A particle size distribution of $d_{10}=5.7$ μm, $d_{50}=24$ μm, and $d_{90}=71$ μm was obtained for this product. This product is particularly well suited to fine polishing of surfaces. An example of such surfaces are the surfaces of acrylic polymer used for dentures or parts fabricates using a polymer set forth in the Industrial Materials Reference.

Example 3

Harborlite® PA 4000 (Harborlite Corporation, Santa Barbara, Calif.) (See Example 2 for Specifications) was screened through a 200-mesh sieve, with the material passing through the sieve retained. A particle size distribution of $d_{10}=5.5$ μm, $d_{50}=23$ μm, and $d_{90}=60$ μm. This product is particularly well suited to fine polishing of surfaces, where greater top size control of the polish is desired to avoid scratches. An example of such surfaces are the surfaces of parts formed of "engineering materials" set forth in the Industrial Materials Reference.

Example 4

Harborlite® PA 1000 (Harborlite Corporation, Santa Barbara, Calif.) (See Example 1 for Specification) was screened over 140-mesh sieve, and captured on a 200-mesh sieve as the product, with the material passing through the sieves discarded. A particle size distribution of $d_{10}=78$ μm, $d_{50}=110$ μm, and $d_{90}=162$ μm was obtained for this product. This product is particularly well suited to coarse polishing of highly irregular surfaces, but where greater top size control is desired to avoid scratches. An example of such surfaces are the surfaces of parts formed of "engineering materials" as set forth in the Industrial Materials Reference and surfaces of a CRT tube. This composition can also be used in a prophy paste.

Example 5

Harborlite® PA 1000 (Harborlite Corporation, Santa Barbara, Calif.) (See Example 1 for Specification) was screened over 140-mesh sieve, with the material passing through the sieves discarded.

A particle size distribution of $d_{10}=110$ μm, $d_{50}=152$ μm, and $d_{90}=218$ μm was obtained for this product. This product is particularly well suited for very fast coarse polishing of manufactured products, e.g. parts formed of "engineering materials" as set forth in the Industrial Materials Reference.

Also, this composition has utility for rapid polishing of surfaces of a CRT tube.

Example 6

Harborlite® 1000 (Harborlite Corporation, Santa Barbara, Calif.) (See Example 1 for Specification) was screened through a 100-mesh sieve, and Harborlite® 4000 (See Example 2 for Specification) was also screened through a 100-mesh sieve, with the material passing through the sieves retained. The two portions retained were then combined in a 50:50 proportion by weight to obtain the desired particle size distribution of $(d_{10})=9$ μm, $(d_{50})=45$ μm, and $(d_{90})=122$ μm. A tablet of High Impact Hi-I® dental acrylic (Fricke Dental International, Inc., Villa Park, Ill.) having an initial 85° Sheen of 4.7 was polished with the unexpanded perlite ore abrasive polishing product in a water slurry on a buffing wheel. Polishing forces were in the range of about 0.2 kg/cm$^2$ (200 kg/cm$^2$) to about 0.5 kg/cm$^2$ (500 kg/cm$^2$). The tablet achieved a high gloss, having a 85° Sheen of 61.2.

The Following are examples of methods for preparing specific unexpanded perlite ore polishing compositions.

Example 7

Methods for Preparing a Unexpanded Perlite Ore Polishing Composition for Surfaces Requiring a High Polish Fine unexpanded perlite ore polishing composition obtained from crushing and milling of unexpanded perlite ore, such as Harborlite® PA-4000 or Harborlite® PA-1000 (Harborlite Corporation, Santa Barbara, Calif.), are suitable as feed material to prepare the unexpanded perlite ore polishing composition (See Examples 1 and 2 for Specifications). One useful method of preparing the unexpanded perlite ore polishing composition is by screening the feed material through a 100-mesh (150 μm) screen to remove oversize particles that would otherwise scratch the surfaces being polished. Other methods to remove oversize grains of particles and to develop a selected distribution of particle sizes of unexpanded perlite ore suitable for practicing this invention include air classifying, mechanical classifying, air tabling, cycloning, hydrocycloning, riffling, rocking, elutriating, centrifuging or sedimenting. The use of the term "selected distribution of particle size", as used herein, envisions using any of the above methods for developing a base material, a first base unexpanded perlite ore material, a second base unexpanded perlite ore material or a blend of the above having grains of a selected distribution of unexpanded perlite ore size.

Examples of materials requiring a highly polished surface which can be highly polished using the teachings of the present invention include optical glass and lenses glass, provided the glass is equal to or less than the hardness of the unexpanded perlite ore polishing composition.

Example 8

Methods of using the Unexpanded Perlite Ore Polishing Composition for Acrylic Polymers The unexpanded perlite ore polishing composition for polymers described above may be used in a manner analogous to the currently available abrasive polishing products. It is particular useful when used as a grit polish for dentures, in which it may be applied in a water slurry on a buffing wheel under an appropriate abrasive force or polishing force.

The preferred embodiment for practicing this invention is for the polishing of dentures using the unexpanded perlite ore polishing composition of Example 2 above. However, it is envisioned that the unexpanded perlite ore polishing composition in substantially the same embodiment or a variations thereof including, without limitation the examples described herein, may have utility for polishing surface of "engineering materials" specified in the Industrial Materials Reference and surfaces of other known materials as described in all of the references set forth above. It will be appreciated that various alterations and modifications may be made to the unexpanded perlite ore polishing composition to enhance the functional characteristics thereof. All such variations and modifications should be considered to fall within the scope of the invention as broadly hereinbefore described and as claimed hereafter.

The final polishing composition of the unexpanded perlite ore polishing composition of the present invention has a distribution of particle sizes having a greater number of grains of unexpanded perlite ore having a smaller size than the number of grains of unexpanded perlite ore having a smaller particle sizes in the selected distribution in the base material or base composition as discussed above. It is desirable that the grains of unexpanded perlite ore have a distribution of particle size in the range of about 20 µm to about 100 µm. The preferred range would be about 20 µm to about 50 µm. It is preferred that substantially all of the grains of unexpanded perlite ore in the final polishing composition be below 50 µm.

The teachings of the present invention has utility for use as a dentifrice such as a dental prophalaxis paste. The dental prophalaxis paste comprises a composition having a base material having grains of unexpanded perlite ore of a selected distribution of particle sizes which undergo fracturing of the grains as a function of an abrasive force applied to the base material. The selected distribution of particle sizes include a significant volume of grains of unexpanded perlite ore having a particle size of less than about 245 µm. The base material is responsive to an abrasive force being applied thereto during polishing resulting in continued fracturing of the grains of unexpanded perlite ore to yield a final polishing composition having a sufficiently low level of abrasiveness under said abrasive force making it suitable for use in polishing. The composition would include a paste component.

Known paste components include a preselected amount and grade of pumice, clay, glycerin and, alternatively, may include an amount of triclosan for providing antimicrobial properties. The pumice and/or clay in the paste component may be replaced by the unexpanded perlite ore composition of the present invention. Also, the pumice and/or clay, or both, could be retained in the paste as a component and the unexpanded perlite ore composition may be added as an additional component to the paste.

The teachings of the present invention could be used as a strip material for polishing teeth. The strip material for polishing teeth comprises a strip member configured for polishing teeth and a base material incorporated into the strip materials wherein the base material includes grains of unexpanded perlite ore of a selected distribution of particle sizes which undergo fracturing of the grains as a function of an abrasive force applied to the base material. The selected distribution of particle sizes includes a significant volume of grains of unexpanded perlite ore having a particle size of less than about 245 µm. The base material is responsive to an abrasive force being applied thereto during polishing resulting in continued fracturing of the grains of unexpanded perlite ore to yield a final polishing composition having a sufficiently low level of abrasiveness under the abrasive force making it suitable for use in polishing. The strip material may comprise a strip member comprising a material configured for use as dental floss or for use as dental tape.

Abrasive forces for practicing this invention may be in the range of about 0.1 kg/cm$^2$ (100 kg/cm$^2$) to about 0.7 kg/cm2 (700 kg/cm$^2$). The preferred range is in the order of about 0.2 kg/cm$^2$ (200 kg/cm$^2$) to about 0.5 kg/cm$^2$ (500 kg/cm$^2$).

Another use of the compositions of the present invention is that the compositions, such as those set forth in Examples 4 and 5 above, can be used to replace use of pumice for polishing in steps where a coarse grade pumice is first used to polish the surface of a CRT which is then followed by polishing using a medium grade pumice in that a single composition can be used in lieu of separate steps of polishing using different grades of pumice.

Acrylic Dentures Polishing Compositions And Methods

In the field of dentistry, the fabrication and polishing of dentures uses a wide variety of polishing agents and compounds to obtain a desired surface finish, polish and shine. Pumice and polycril are examples of presently used materials as polishing agents and compounds.

Pumice is a rock forth formed by the extreme puffing of liquid lava by expanding gases liberated from solution in the lava prior to and during solidification. Pumice is also known as foam, pumice stone pumicite and volcanic foam.

Polycril is a diatomaceous earth calcined with a fluxing agent, typically called flux-calcined diatomite.

Shine from use of a polishing agent or compounds can be measured. For purpose of this invention, "shine" is measured at 85° specular reflectance using a BYK Gardner USA micro-TRI gloss meter. On acrylic dentures, use of a course pumice produces a shine of about 33 and use of a polycril produce a shine of about 48.

The unexpanded perlite ore polishing composition of the present invention is ideally suited for use as an acrylic denture polishing composition. The following examples are provided as exemplary.

Example 9

The base material for this acrylic denture polishing composition is fabricated from Harborlite Perlite Grade PA-1000 described above in Example 1, using appropriate sieves to obtain a base material having the following product distribution criteria:

| | | |
|---|---|---|
| ($d_{10}$) | 92.0 µm | Rounded about 92 µm |
| ($d_{50}$) | 146.0 µm | Rounded about 146.0 µm |
| ($d_{90}$) | 229.0 µm | Rounded about 229.0 µm |

The ($d_{90}$) is about 229 µm.

The degradation of the 229 Composition to obtain the desired polishing results appears to have a final particle size distribution as follows:

| | | |
|---|---|---|
| ($d_{10}$) | 68.59 µm | Rounded about 69 µm |
| ($d_{50}$) | 100.31 µm | Rounded about 100 µm |
| ($d_{90}$) | 153.46 µm | Rounded about 154 µm |

The base material may be combined with a known paste component having pumice, clay and glycerin. Alternatively, the paste component may include an amount of triclosan for providing antimicrobial properties.

The resulting acrylic denture polishing composition for this Example is referred to as the "229 Composition".

The testing apparatus comprised forming dental acrylic into plates having a polishing area of 12 square centimeters ($cm^2$) using Hi-I High Impact Denture Material Special Fibered #1 Self Curing (heat cured) from Fricke International Inc. The plates were polished on a fabric buff.

The 229 Composition can be used by the user for polishing an acrylic denture until the desired surface finish is obtained, which is independent of time.

The testing apparatus was used with the 229 Composition to determine the time needed for the 229 Composition to obtain the same level of shine for competitive materials; namely course pumice and polycril, as examples. When a given surface area is to be used for polishing, as in the testing apparatus described above, the polishing process is normalized and unites of speed can be developed.

Using the above criteria and testing apparatus, the following results were developed for shine for the: (i) 229 Composition; (ii) course pumice and (iii) polycril.

(A) 229 Composition and Course Pumice:

Course pumice maximum shine is about 33. The 229 Composition maximum shine is about 70.

Coarse Pumice achieved maximum shine in about 30 seconds giving a speed of about 0.40 $cm^2$/sec using the testing apparatus.

The 229 Composition achieved the substantially equivalent shine of Course Pumice in about 8.6 seconds giving a speed of about 1.40 $cm^2$/sec using the testing apparatus.

Thus, the 229 Composition polishes about 3.5 times (1.40 $cm^2$/sec divided by 0.40 $cm^2$/sec) faster than course pumice.

(B) 229 Composition and Polycril.

Polycril maximum shine is about 48. The 229 Compostion maximum shine is about 70.

Polycril achieved maximum shine in about 30 seconds giving a speed of about 0.40 $cm^2$/sec using the testing apparatus.

The 229 Composition achieved the substantially equivalent shine of polycril in about 13 seconds giving a speed of about 0.94 $cm^2$/sec using the testing apparatus.

Thus, the 229 Composition polishes about 2.4 times (0.94 $cm^2$/sec divided by 0.40 $cm^2$/sec) faster than polycril.

Example 10

The base material for this acrylic denture polishing composition is fabricated from Harborlite Perlite Grade PA-1000 described above in Example 1, using appropriate sieves to obtain a base material having the following product distribution criteria:

| | | |
|---|---|---|
| ($d_{10}$) | about 54.042 µm | Rounded about 54.0 µm |
| ($d_{50}$) | about 82.791 µm | Rounded about 83 µm |
| ($d_{90}$) | about 127.797 µm | Rounded about 128 µm |

The ($d_{90}$) is about 101 µm depending on the ore.

The degradation of the 101 Composition to obtain the desired polishing results appears to have a final particle size distribution as follows:

| | | |
|---|---|---|
| ($d_{10}$) | 19.9 µm | Rounded about 20 µm |
| ($d_{50}$) | 47.9 µm | Rounded about 48 µm |
| ($d_{90}$) | 101.3 µm | Rounded about 101 µm |

The base material may be combined with a known paste component having pumice, clay and glycerin. Alternatively, the paste component may include an amount of triclosan for providing antimicrobial properties.

The resulting acrylic denture polishing composition for this Example is referred to as the "101 Composition".

The testing apparatus described in Example 9 was used.

The 101 Composition can be used by the user for polishing an acrylic denture until the desired surface finish is obtained, which is independent of time.

The testing apparatus was used with the 101 Composition to determine the time needed for the 101 Composition to obtain the same level of shine for competitive materials; namely medium pumice, polycril and Dazzle Brand polish, as examples. When a given surface area is to be used for polishing, as in the testing apparatus described above, the polishing process is normalized and units of speed can be developed.

Using the above criteria and testing apparatus, the following results were developed for shine for the: (i) 101 Composition; (ii) medium pumice; (iii) polycril.

(A) 101 Composition and Medium Pumice:

Medium pumice maximum shine is about 58. The 101 Composition maximum shine is about 85.

Medium Pumice achieved maximum shine in about 30 seconds giving a speed of about 0.40 cm²/sec using the testing apparatus.

The 101 Composition achieved the substantially equivalent shine of Course Pumice in about 11.0 seconds giving a speed of about 1.10 cm²/sec using the testing apparatus.

Thus, the 101 Composition polishes about 2.75 times (1.10 cm²/sec divided by 0.40 cm²/sec) faster than medium pumice.

(B) 101 Composition and Polycril.

Polycril maximum shine is about 48. The 101 Composition maximum shine is about 86.

Polycril achieved maximum shine in about 30 seconds giving a speed of about 0.40 cm²/sec using the testing apparatus.

The 101 Composition achieved the substantially equivalent shine of Polycril in about 8.7 seconds giving a speed of about 1.38 cm²/sec using the testing apparatus.

(C) 101 Composition and Dazzle Polish.

Dazzle polish maximum shine is about 70. The 101 Composition maximum shine is about 86.

Dazzle polish achieved maximum shine in about 75 seconds giving a speed of about 0.16 cm²/sec using the testing apparatus.

The 101 Composition achieved the substantially equivalent shine of Dazzle polish in about 13.9 seconds giving a speed of about 0.88 cm²/sec using the testing apparatus.

Thus, the 101 Composition polishes about 5.5 times (0.88 cm²/sec divided by 0.16 cm²/sec) faster than Dazzle polish.

In summary, the acrylic denture polishing composition of the present invention comprises a base material having grains of unexpanded perlite ore of a selected distribution of particle sizes which undergo fracturing of the grains as a function of an abrasive force applied to the base material. The selected distribution of particle sizes includes a significant volume of grains of unexpanded perlite ore having a ($d_{90}$) particle size in a range of about 101 µm to about 229 µm. The base material is responsive to an abrasive force being applied thereto during polishing of acrylic dentures resulting in continued fracturing of the grains of unexpanded perlite ore to yield a final polishing composition having a sufficiently low level of abrasiveness under the abrasive force making it suitable for use in polishing.

Cathode Ray Tube Surface Polishing Composition And Method

In the cathode ray tube ("CRT") fabrication field, the polishing of the CRT glass optical or viewing surface is performed using a wide variety of polishing agents and compounds to obtain a desired surface smoothness and finish. Pumice is typically used as the polishing agent in combination with a mechanical or automated CRT surface polishing system.

One example of pumice used for polishing a CRT optical or viewing surface is Hess Pumice offered for sale and sold by Hess Pumice Products, Inc. of Malad, Id. The significant key features of the Hess Pumice include: (i) Purity content in the order of 98%-99%, depending on grade; (ii) Low unit weight or bulk density in the order of 40 to 45 lbs per cubic foot, depending on grade; (iii) MOHS of between 5.5 and 6.0 and (iv) pH of 7.2.

The cathode ray tube surface polishing composition of the present invention comprises a base material having grains of unexpanded perlite ore of a selected distribution of particle sizes which undergo fracturing of the grains as a function of an abrasive force applied to the base material. The selected distribution of particle sizes include a significant volume of grains of unexpanded perlite ore having a ($d_{90}$) particle size in a range of about 159 µm to about 244 µm. The base material is responsive to an abrasive force being applied thereto during polishing of the CRT surface resulting in continued fracturing of the grains of unexpanded perlite ore to yield a final polishing composition having a sufficiently low level of abrasiveness under the abrasive force making it suitable for use in polishing.

The base material for this cathode ray tube surface polishing composition may be fabricated from unexpanded perlite ore using Harborlite Perlite Grade PA-1000, described above in Example 1 and Harborlite Perlite Grade PA-4000, described above in Example 2.

By selecting a sieve of a predetermined mesh size, a desired particle size distribution can be obtained for the cathode ray tube polishing composition. The following examples are provided.

Example 11

Harborlite® PA 1000 (Harborlite Corporation, Santa Barbara, Calif.) was screened through a sieve having an appropriate size, with the material passing through the sieve retained to produce a base material having a particle size distribution as follows:

| | | |
|---|---|---|
| ($d_{10}$) | 31.2 µm | Rounded about 31 µm |
| ($d_{50}$) | 76.0 µm | Rounded about 76 µm |
| ($d_{90}$) | 158.6 µm | Rounded about 159 µm |

This product is particularly well suited to fine polishing of cathode ray tube glass surfaces. The resulting cathode ray tube polishing composition in this Example is referred to as the "CRT Fine Composition".

The CRT Fine Composition can be used by the user for polishing a cathode ray tub surface until the desired surface finish is obtained, which is independent of time.

The CRT Fine Composition was used to determine the time needed for the CRT Fine Composition to obtain the same level of sheen as the Hess Pumice.

Using the above criteria, the following results were developed for the CRT Fine Composition and the Hess Pumice.

Figure 12:
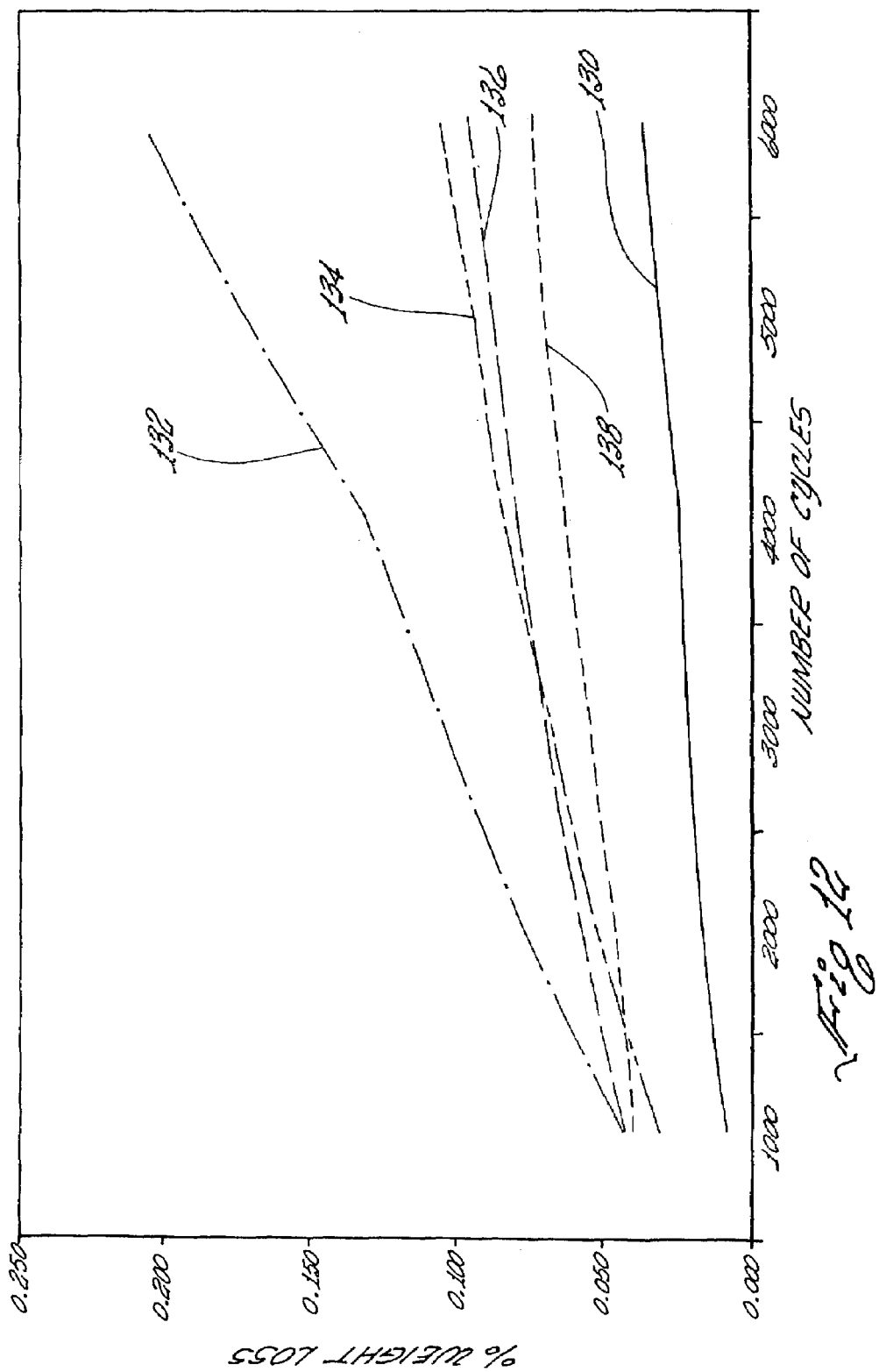
FIG. 12 is a graph of percentage weight loss verses number of cycles for polishing a CRT glass surface using pumice and four (4) grades of CRT polishing composition using the teachings of this invention.

(A) CRT Fine Composition and Hess Pumice:

FIG. 12 is a graph showing percentage weight loss of glass removed from the glass surface of a CRT plotted as a function of number of cycles of a polishing apparatus for pumice which is shown by solid line 130, and the CRT Fine Composition of the present invention shown by dashed line 138. Based on the percentage weight loss using the CRT Fine Composition as compared to the percentage weight loss using pumice, the CRT Fine Composition removes the glass faster than pumice.

The CRT Fine Composition can achieved the substantially equivalent sheen of the Hess Pumice in less time due to the ability of the CRT Fine Composition to remove more glass from a CRT glass surface per unit time.

Example 12

Harborlite® PA 1000 (Harborlite Corporation, Santa Barbara, Calif.) was screened through a sieve having an appropriate size, with the material passing through the sieve retained to produce a base material having a particle size distribution as follows:

| | | |
|---|---|---|
| ($d_{10}$) | 63.6 μm | Rounded about 64 μm |
| ($d_{50}$) | 135.8 μm | Rounded about 136 μm |
| ($d_{90}$) | 248.3 μm | Rounded about 248 μm |

This product is particularly well suited to medium polishing of cathode ray tube glass surfaces. The resulting cathode ray tube polishing composition in this Example is referred to as the "CRT Medium Composition".

The CRT Medium Composition can be used by the user for polishing a cathode ray tub surface until the desired surface finish is obtained, which is independent of time.

The CRT Medium Composition was used to determine the time needed for the CRT Fine Composition to obtain the same level of sheen as the Hess Pumice.

Using the above criteria, the following results were developed for the CRT Medium Composition and the Hess Pumice.

(A) CRT Medium Composition and Hess Pumice:

FIG. 12 is a graph showing percentage weight loss of glass removed from the glass surface of a CRT plotted as a function of number of cycles of a polishing apparatus for pumice which is shown by solid line 130, and the CRT Medium Composition of the present invention shown by the line composed of a short dash and a long dash 132. Based on the percentage weight loss using the CRT Fine Composition as compared to the percentage weight loss using pumice, the CRT Fine Composition removes the glass faster than pumice.

The CRT Medium Composition can achieve the substantially equivalent sheen of the Hess Pumice in less time due to the ability of the CRT Medium Composition to remove more glass from a CRT glass surface per unit time.

Example 13

Harborlite® PA 1000 (Harborlite Corporation, Santa Barbara, Calif.) was screened through a sieve having an appropriate size, with the material passing through the sieve retained to produce a base material having a particle size distribution as follows;

| | | |
|---|---|---|
| ($d_{10}$) | 105.7 μm | Rounded about 106 μm |
| ($d_{50}$) | 163.9 μm | Rounded about 164 μm |
| ($d_{90}$) | 244.3 μm | Rounded about 244 μm |

This product is particularly well suited to course polishing of cathode ray tube glass surfaces. The resulting cathode ray tube polishing composition in this Example is referred to as the "CRT Course Composition".

This product is particularly well suited to course polishing of cathode ray tube glass surfaces. The resulting cathode ray tube polishing composition in this Example is referred to as the "CRT Course Composition".

The CRT Course Composition can be used by the user for polishing a cathode ray tub surface until the desired surface finish is obtained, which is independent of time.

The CRT Course Composition was used to determine the time needed for the CRT course Composition to obtain the same level of sheen as the Hess Pumice.

Using the above criteria, the following results were developed for the CRT Course Composition and the Hess Pumice.

(A) CRT Course Composition and Hess Pumice:

FIG. 12 is a graph showing percentage weight loss of glass removed from the glass surface of a CRT plotted as a function of number of cycles of a polishing apparatus for pumice which is shown by solid line 130, and the CRT Course Composition of the present invention shown by the line formed of long dashes 138. Based on the percentage weight loss using the CRT Course Composition as compared to the percentage weight loss using pumice, the CRT Course Composition removes the glass faster than pumice.

The CRT Course Composition can achieved the substantially equivalent sheen of the Hess Pumice in less time due to the ability of the CRT Course Composition to remove more glass from a CRT glass surface per unit time.

Example 14

Harborlite® PA 1000 (Harborlite Corporation, Santa Barbara, Calif.) was screened through a sieve having an appropriate size, with the material passing through the sieve retained to produce a base material having a particle size distribution as follows:

| | | |
|---|---|---|
| ($d_{10}$) | 63.6 μm | Rounded about 64 μm |
| ($d_{50}$) | 119.3 μm | Rounded about 119 μm |
| ($d_{90}$) | 192.2 μm | Rounded about 194 μm |

This product is particularly well suited to fine polishing of cathode ray tube glass surfaces. The resulting cathode ray tube polishing composition in this Example is referred to as the "CRT Special Composition".

This product is particularly well suited to fine polishing of cathode ray tube glass surfaces, where greater top size control of the polish is desired to avoid scratches being formed in the final polished surface. The resulting cathode ray tube polishing composition in this Example is referred to as the "CRT Special Composition".

The CRT Special Composition can be used by the user for polishing a cathode ray tub surface until the desired surface finish is obtained, which is independent of time.

The CRT Special Composition was used to determine the time needed for the CRT Special Composition to obtain the same level of sheen as the Hess Pumice.

Using the above criteria, the following results were developed for the CRT Special Composition and the Hess Pumice.

(A) CRT Special Composition and Hess Pumice:

FIG. 12 is a graph showing percentage weight loss of glass removed from the glass surface of a CRT plotted as a function of number of cycles of a polishing apparatus for pumice which is shown by solid line 130 and the CRT Special Composition of the present invention shown by the line composed of two short and one long dashes 134. Based on the percentage weight loss using the CRT Fine Composition as compared to the percentage weight loss using pumice, the CRT Special Composition removes the glass faster than pumice.

The CRT Special Composition can achieved the substantially equivalent sheen of the Hess Pumice in less time due to the ability of the CRT Special Composition to remove more glass from a CRT glass surface per unit time. Also, the resulting polished cathode ray tube polished glass surface had less scratches as compare to the cathode ray tube glass surfaces polished with Hess Pumice.

Acrylic Dental Polishing Compositions and Cathode Ray Tube Polishing Compositions With Filler Material The acrylic dental polishing compositions and cathode ray tube polishing compositions described above can be combined with a filler material comprising grains of expanded perlite material having a density in the range of about 2 lbs. per cubic feet and about 20 lbs. per cubic feet. The density of expanded perlite material used in this invention is preferably in the range of about 7 lbs. per cubic feet and about 15 lbs. per cubic feet. The base material used for the unexpanded perlite ore of a selected distribution of particle sizes used in this invention has a bulk density preferably in the range of about 65.0 to about 70.0 lbs. per cubic foot.

Unexpanded Perlite Ore Polishing

Composition Safety Advantages

If a product contains a concentration of crystalline silica of 0.1% or more, certain countries consider this level as hazardous and require hazard warning language be included in the Material Safety Data Sheets. For other countries, a concentration of crystalline silica of 1% is the threshold for the material being deemed as hazardous requiring hazard warning language on Material Safety Data Sheets. One example of a typical hazardous warning language is a follows:

"This product contains crystalline silica (CS) which is considered a hazard by inhalation. IARC has classified inhalation of CS as carcinogen for humans (Group 1). CS is listed by NTP as a known human carcinogen. Inhalation of CS is also a known cause of silicosis, a noncancerous lung disease."

Generally, pumice is known to have a concentration of crystalline silica in excess of 0.1% which requires a user to consider the safety issues described above.

The above described acrylic dental polishing compositions and cathode ray tube polishing compositions contain less than 0.1% (w/w) crystalline silica. As such, a user is not required to consider the safety issues described above which represents a significant advantage with respect to the safety and utility of the present invention.

Other Unexpanded Perlite Ore Polishing Composition Having Selected Particle sizes It is envisioned that the use of the unexpanded perlite ore composition as a microblasting agent would preferably utilize a composition generally limited to a maximum particle size of about 100 μm or less. Such unexpanded perlite ore compositions can be used in lieu of the known microblasting agents which typically have a median particle size of about 25 μm and 50 μm, respectively, for microetching, as opposed to polishing, of aluminum metal and stainless steel for manufacture of components such as, for example, jet turbine engines. In addition, the composition of the present invention can be used in lieu of or in combination with alumina which is used to etch enamel in highly specialized microblasting applications.

In an overview, it is envisioned that the compositions of the present invention could have a distribution of particle sizes including a significant volume of grains of unexpanded perlite ore having a particle size of greater than about 222 μm if the polishing process can tolerate use of the same, such as for example, scratching of the surface due to coarse particle size or that the polishing process can be continued, with concern for time of polishing, to yield a final polishing composition having a sufficiently low level of abrasiveness under said abrasive force making it suitable for use in polishing.

As a general principal, a polishing composition having unexpanded perlite ore having particle sizes greater than the ranges disclosed and taught herein will take longer to decompose. Conversely a polishing composition having unexpanded perlite ore having particle sizes smaller than the ranges disclosed and taught herein will take less time to decompose.

The examples disclosed herein are intended to cover such applications discussed therein, and it is envisioned that such other uses of a unexpanded perlite ore composition will become apparent to those skilled-in-the-art and such uses are envisioned to be within the teaching of the present invention.

All such uses, variations, modifications and the like are anticipated to be within the scope of this invention.

What is claimed is:

1. A method for polishing a surface of an acrylic denture comprising:
    applying to the surface of an acrylic denture a polishing composition comprising a paste comprising grains of perlite ore consisting essentially of unexpanded perlite ore having a ($d_{90}$) particle size ranging from about 101 to about 229 μm, and
    applying an abrasive force to the paste,
    wherein the abrasive force results in continued fracturing of the grains of perlite ore to yield a final polishing composition having a level of abrasiveness suitable for use in polishing the surface of an acrylic denture.

2. The method of claim 1, wherein continued fracturing of the grains of perlite ore consisting essentially of unexpanded perlite ore yields a final polishing surface having a shine of about 70 measured at 85° specular reflectance using a BYK Gardner USA micro-TRI gloss meter.

3. The method of claim 1, wherein continued fracturing of the grains of perlite ore consisting essentially of unexpanded perlite ore yields a final polishing surface having a shine of about 85 measured at 85° specular reflectance using a BYK Gardner USA micro-TRI gloss meter.

4. A method for polishing a surface of an article comprising
    applying to the surface of an article an unexpanded perlite ore polishing composition comprising a paste comprising grains of perlite ore consisting essentially of unexpanded perlite ore having a ($d_{90}$) particle size ranging from about 101 μm to about 244 μm; and
    applying an abrasive force to said paste,
    wherein the abrasive force results in continued fracturing of the grains of perlite ore to yield a final polishing composition having a level of abrasiveness suitable for use in polishing the surface of an article.

5. A method for polishing a glass surface comprising:
applying to the glass surface a polishing composition comprising a paste comprising grains of perlite ore consisting essentially of unexpanded perlite ore having a ($d_{90}$) particle size ranging from about 159 to about 244 μm, and
applying an abrasive force to the paste,
wherein the abrasive force results in continued fracturing of the grains of perlite ore to yield a final polishing composition having a level of abrasiveness suitable for use in polishing the glass surface.

6. The method of claim 5, wherein the glass is chosen from cathode ray tubes, television tubes, eyeglasses, photographical optical components, and laser optical components.

7. The method of claim 5 wherein said final polishing composition has a particle size distribution comprising a greater number of smaller grains with sizes in the range of about 20 μm to about 120 μm than in said paste.

8. The method of claim 5 wherein said ore has a ($d_{90}$) particle size of about 159 μm.

9. The method of claim 5 wherein said ore has a ($d_{90}$) particle size of about 244 μm.

10. The method of claim 5 wherein said ore has a ($d_{90}$) particle size of about 192 μm.

11. The method of claim 8 wherein said ore has a ($d_{50}$) particle size of about 76 μm.

12. The method of claim 9 wherein said ore has a ($d_{50}$) particle size of about 136 μm.

13. The method of claim 5 wherein said ore has a ($d_{50}$) particle size of about 164 μm.

14. The method of claim 10 wherein said ore has a ($d_{50}$) particle size of about 120 μm.

15. The method of claim 11 wherein said ore has a ($d_{10}$) particle size of about 31 μm.

16. The method of claim 12 wherein said ore has a ($d_{10}$) particle size of about 64 μm.

17. The method of claim 5 wherein said ore has a ($d_{10}$) particle size of about 106 μm.

18. The method of claim 14 wherein said ore has a ($d_{10}$) particle size of about 64 μm.

19. A surface treating method comprising:
providing a surface to be treated;
applying an unexpanded perlite ore polishing composition comprising grains of perlite ore consisting essentially of unexpanded perlite ore having a ($d_{90}$) particle size ranging from about 101 μm to about 248 μm, said grains of perlite ore having a hardness greater than the hardness of the surface; and
applying an abrasive force to the grains of perlite ore,
wherein the abrasive force results in continued fracturing of the grains of perlite ore to yield a final polishing composition having a level of abrasiveness suitable for polishing the surface.

20. The surface treating method of claim 19 further comprising the steps of providing a source of an abrasive force and a source of a perlite ore polishing composition.

* * * * *